(12) United States Patent
Placha et al.

(10) Patent No.: US 10,912,756 B2
(45) Date of Patent: Feb. 9, 2021

(54) METHOD FOR THE TREATMENT OF HUMAN MELANOMA

(71) Applicant: UNIWERSYTET JAGIELLONSKI, Cracow (PL)

(72) Inventors: Wojciech Placha, Cracow (PL); Jacek Zagajewski, Cracow (PL); Malgorzata Szczygiel, Cracow (PL); Monika Piwowar, Cracow (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 0 days.

(21) Appl. No.: 16/479,397

(22) PCT Filed: Jan. 19, 2018

(86) PCT No.: PCT/PL2018/050002
§ 371 (c)(1),
(2) Date: Jul. 19, 2019

(87) PCT Pub. No.: WO2018/135959
PCT Pub. Date: Jul. 26, 2018

(65) Prior Publication Data
US 2019/0358194 A1 Nov. 28, 2019

(30) Foreign Application Priority Data
Jan. 19, 2017 (PL) .......................... 420249

(51) Int. Cl.
*A61K 31/351* (2006.01)
*A61P 35/00* (2006.01)
*A61K 33/243* (2019.01)
*A61K 31/197* (2006.01)
*A61K 31/337* (2006.01)

(52) U.S. Cl.
CPC .......... *A61K 31/351* (2013.01); *A61K 31/197* (2013.01); *A61K 31/337* (2013.01); *A61K 33/243* (2019.01); *A61P 35/00* (2018.01); *A61K 2300/00* (2013.01)

(58) Field of Classification Search
CPC .............................. A61K 31/351; A61P 35/00
USPC ........................................................ 514/460
See application file for complete search history.

(56) References Cited

PUBLICATIONS

Holstein et al., "Synergistic Interaction of Lovastatin and Paclitaxel in Human Cancer Cells", Molecular Cancer Therapeutics, vol. 1, No. 2, pp. 141-149 (Dec. 2001).*
Follet et al.,"The association of statins and taxanes: an efficient combination trigger of cancer cell apoptosis", British Journal of Cancer, vol. 106, No. 4, pp. 685-692 (Feb. 2012).*

Robinson et al., "Preclinical evaluation of statins as a treatment of ovarian cancer", Gynecologic Oncology, vol. 129, No. 2, pp. 417-424 (May 2013).*
Chen et al., "Mechanistic Study of Inhibitory Effects of Atorvastatin and Docetaxel in Combination of Prostate Cancer", Cancer Genomics & Proteomics, vol. 13, No. 2, pp. 151-160 (Mar.-Apr. 2013).*
Kaitlyn M. Gayvert, Omar Aly, James Platt, Marcus W. Bosenberg, David F. Stem, Olivier Elemento. A Computational Approach for Identifying Synergistic Drug Combinations. PLOS Computational Biology, Jan. 13, 2017, 13(1):e1005308, pp. 1-11. <DOI :10.1371/journal.pcbi .1005308>.
Iara F Kretzer, Durvanei A Maria, Maria C Guido, Thais C Contente, Raul C Maranhao. Simvastatin increases the antineoplastic actions of paclitaxel carried in lipid nanoemulsions in melanoma-bearing mice. International Journal of Nanomedicine, Mar. 7, 2016, 11, pp. 885-904. <DOI :10.2147 /IJN.S88546>.
Sharon A Glynn, Dermot O'Sullivan, Alex J Eustace, Martin Clynes and Norma O'Donovan. The 3-hydroxy-3-methylglutaryl-coenzyme A reductase inhibitors, simvastatin, lovastatin and mevastatin inhibit proliferation and invasion of melanoma cells. BMC Cancer, Jan. 16, 2008, 8:9, pp. 1-9. <DOI: 10.1186/1471-2407-8-9>.
K.B. Tran, S. Kolekar, S.M.F. Jamieson, F.W. Hunter, A. Jabed, D. Li W.R. Wilson, B.C. Baguley, J.H. Shih, C.M. Buchanan, P.R. Shepherd. Effects of statins on melanoma. Annals of Oncology, Dec. 2016, vol. 27, Supplement 9, (abstract). Retrieved from <https://doi.org/10.1093/annonc/mdw589.009>.
Sarah A. Holstein and Raymond J. Hohl. Synergistic interaction of lovastatin and paclitaxel in human cancer cells. Molecular Cancer Therapeutics, Dec. 2001, 1(2), pp. 141-149. Retrieved from <http://mct.aacrjournals.org/content/1/2/141>.
Shaojuan Li and Paul de Souza. Ras isoprenylation and pAkt inhibition by zolendronic acid and fluvastatin enhances paclitaxel activity in T24 bladder cancer cells. Cancer, Feb. 14, 2011, 3(1), pp. 662-674. <D01:10.3390/cancers3010662>.
Ahn KS, Sethi G, Aggarwal BB. Reversal of chemoresistance and enhancement of apoptosis by statins through down-regulation of the NF-kappaB pathway. Biochem Pharmacol., Feb. 15, 2008, 75 (4), pp. 907-913. Epub Oct. 16, 2007. DOI:10.1016/j.bcp.2007.10.010>.
Fol Iet J, Coreas L, Baffet G, Ezan F, Morel F, Simon B, Le Jossic-Corcos C. The association of statins and taxanes: an efficient combination trigger of cancer cell apoptosis. British Journal of Cancer, Feb. 14, 2012, 106(4), pp. 685-692. Epub Jan. 31, 2012. <D0I:10.1038/bjc.2012.6>.
Mhaidat NM, Wang Y, Kiejda KA, Zhang XD, Hersey P. Docetaxel-induced apoptosis in melanoma cells is dependent on activation of caspase-2. Molecular Cancer Therapeutics, 6(2), Feb. 2007, pp. 752-761. <D0I:10.1158/1535-7163.MCT-06-0564>.
Aamdal S, Wolff I, Kaplan S, Paridaens R, Kerger J, Schachter J, Wanders J, Franklin HR, Verweij J. Docetaxel (Taxotere) in advanced malignant melanoma: a phase II study of the EORTC early clinical trials group. European Journal of Cancer, vol. 30A, No. 81 pp. 1061-1064, 1994.

(Continued)

*Primary Examiner* — Kevin E Weddington
(74) *Attorney, Agent, or Firm* — Arrigo, Lee, Guttman & Mouta-Bellum LLP

(57) ABSTRACT

Pharmaceutical composition comprising an aqueous solution of a taxane and an aqueous solution of a hydrophobic statin intended for use in treatment or prevention of human melanoma.

10 Claims, 12 Drawing Sheets

(56) References Cited

PUBLICATIONS

Einzig AI, Hochster H, Wiernik PH, Trump DL, Dutcher JP, Garowski E, Sasloff J, Smith TJ. A phase II study of taxol in patients with malignant melanoma. Investigational New Drugs, Feb. 1991, 9 (1), pp. 59-64, (abstract).

Raghu VK, Beckwitt CH, Warita K, Wells A, Benos PV, Oltvai ZN. Biomarker identification for statin sensitivity of cancer cell lines. Biochem Biophys Res Commun., Jan. 1, 2018, 495(1}, pp. 659-665. Epub Nov. 14, 2017. <DOI:10.1016/j.bbrc.2017.11.065>.

Izabela Broniarek, Wiestawa Jarmuszkiewicz. Statyny a mitochondria. Post~py Biochemii, 62 (2), 2016, pp. 77-84. Retrieved from <http://www.postepybiochemii.pl/pdf/2_2016/77-84.pdf>.

Written Opinion, PCT/PL2018/050002, dated May 25, 2018.

International Search Report, PCT/PL2018/050002, dated May 25, 2018.

\* cited by examiner

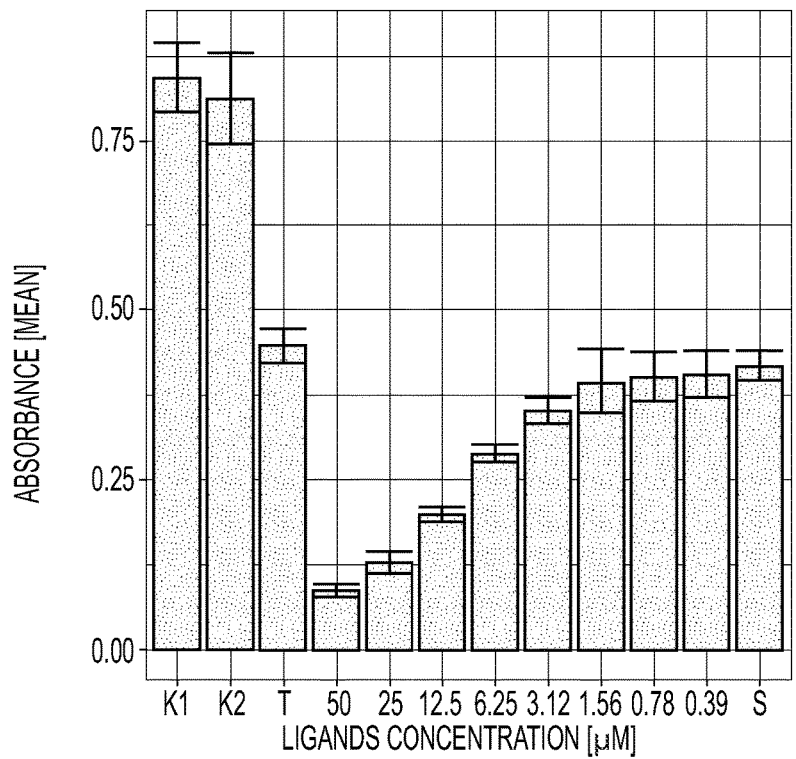

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

T 0.5 µM TAXOL SYSTEM IN RPMI+10%FSC

THE DESIGNATIONS MARKED CONSECUTIVELY FROM 50 TO 0.39 DENOTE DECREASING CONCENTRATIONS OF SIMVASTATIN IN µM ADMINISTERED TOGETHER WITH TAXOL HAVING A CONSTANT CONCENTRATION OF 0.5 µM IN EACH SAMPLE IN THE SEQUENCE

S-SIMVASTATIN ALONE 20 µM

*FIG. 1A*

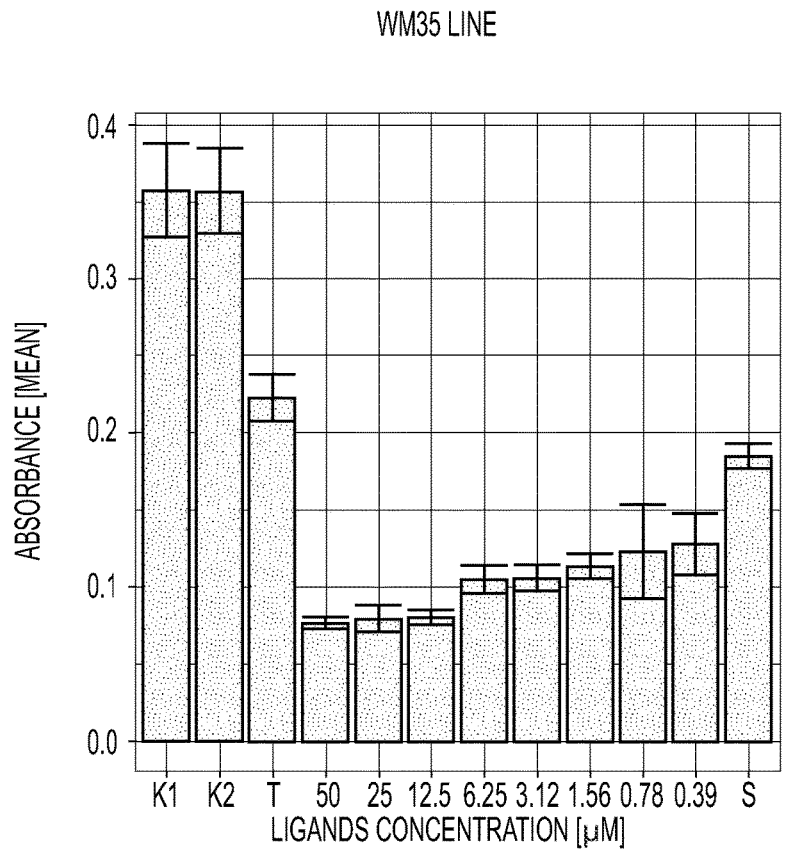

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

T 0.5 µM TAXOL SYSTEM IN RPMI+10%FSC

THE DESIGNATIONS MARKED CONSECUTIVELY FROM 50 TO 0.39 DENOTE DECREASING CONCENTRATIONS OF SIMVASTATIN IN µM ADMINISTERED TOGETHER WITH TAXOL HAVING A CONSTANT CONCENTRATION OF 0.5 µM IN EACH SAMPLE IN THE SEQUENCE

S-SIMVASTATIN ALONE 20 µM

ABSORBANCE [MEAN]

LIGANDS CONCENTRATION

*FIG. 1B*

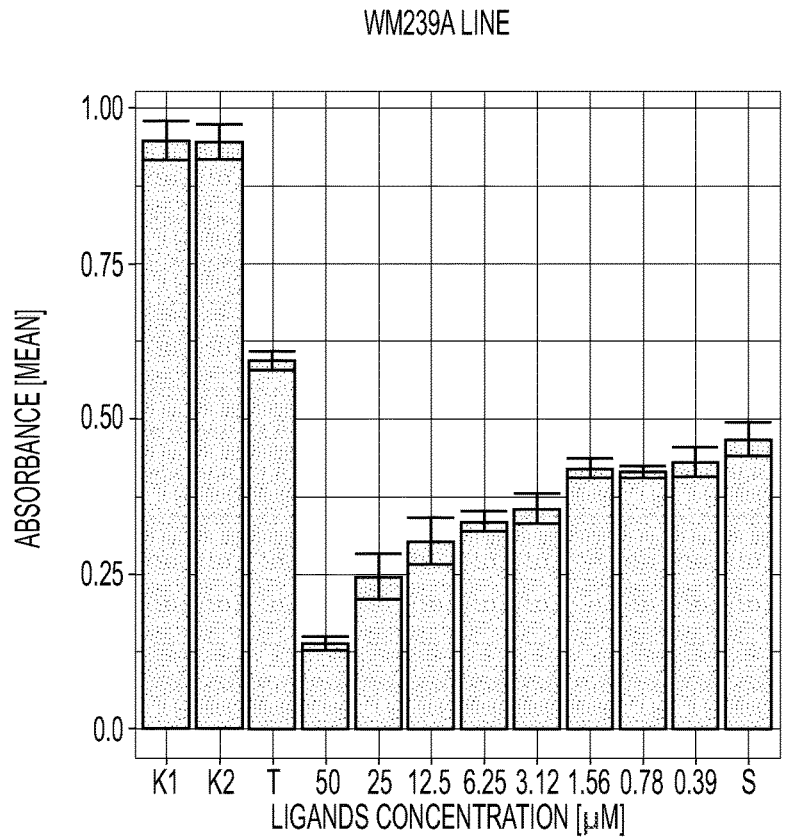

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

T 0.5 µM TAXOL SYSTEM IN RPMI+10%FSC

THE DESIGNATIONS MARKED CONSECUTIVELY FROM 50 TO 0.39 DENOTE DECREASING CONCENTRATIONS OF SIMVASTATIN IN µM ADMINISTERED TOGETHER WITH TAXOL HAVING A CONSTANT CONCENTRATION OF 0.5 µM IN EACH SAMPLE IN THE SEQUENCE

S-SIMVASTATIN ALONE 20 µM

ABSORBANCE [MEAN]

LIGANDS CONCENTRATION

*FIG. 1C*

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

MCT 0.5 μM TAXOL/CISPLATIN/MELPHALAN (MCT) SYSTEM IN RPMI+10%FSC

50 - ... -0,39 -MCT SYSTEM WITH A ADDITION OF SIMVASTATIN IN CONSECUTIVE CONCENTRATIONS

S-SIMVASTATIN

ABSORBANCE [MEAN]

LIGANDS CONCENTRATION

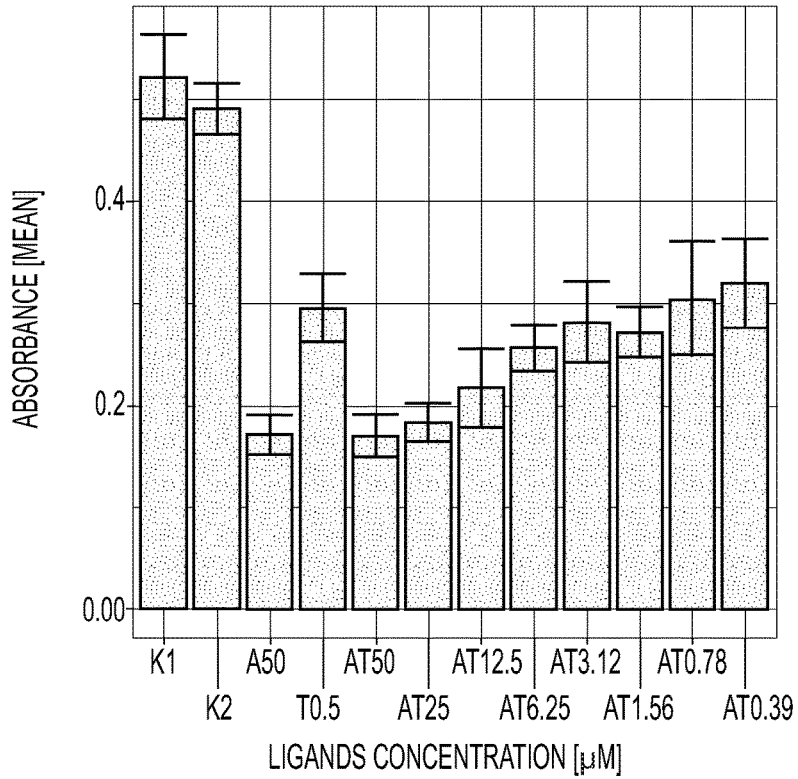

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

A - ATORVASTATIN ALONE, CONCENTRATION 50 μM

T - 0.5 μM TAXOL SYSTEM IN RPMI+10%FSC

THE DESIGNATIONS MARKED CONSECUTIVELY FROM 50 TO 0.39 DENOTE DECREASING CONCENTRATIONS OF ATORVASTATIN [μM] ADMINISTERED TOGETHER WITH TAXOL HAVING A CONSTANT CONCENTRATION OF 0.5 μM IN EACH SAMPLE IN THE SEQUENCE

ABSORBANCE [MEAN]

LIGANDS CONCENTRATION

*FIG. 3*

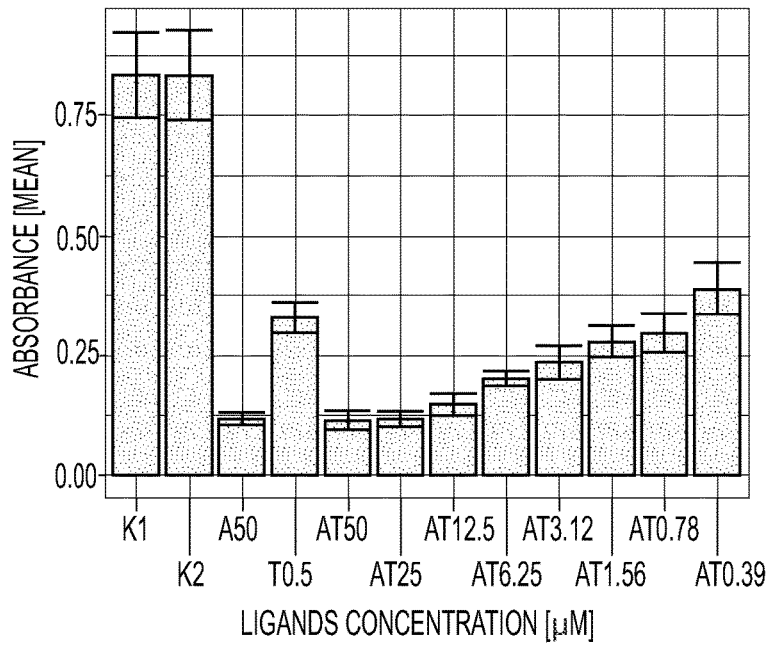

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

A - ATORVASTATIN ALONE, CONCENTRATION 50 μM

T - 0.5 μM TAXOL SYSTEM IN RPMI+10%FSC

THE DESIGNATIONS MARKED CONSECUTIVELY FROM 50 TO 0.39 DENOTE DECREASING CONCENTRATIONS OF ATORVASTATIN [μM] ADMINISTERED TOGETHER WITH TAXOL HAVING A CONSTANT CONCENTRATION OF 0.5 μM IN EACH SAMPLE IN THE SEQUENCE

ABSORBANCE [MEAN]

LIGANDS CONCENTRATION

*FIG. 4*

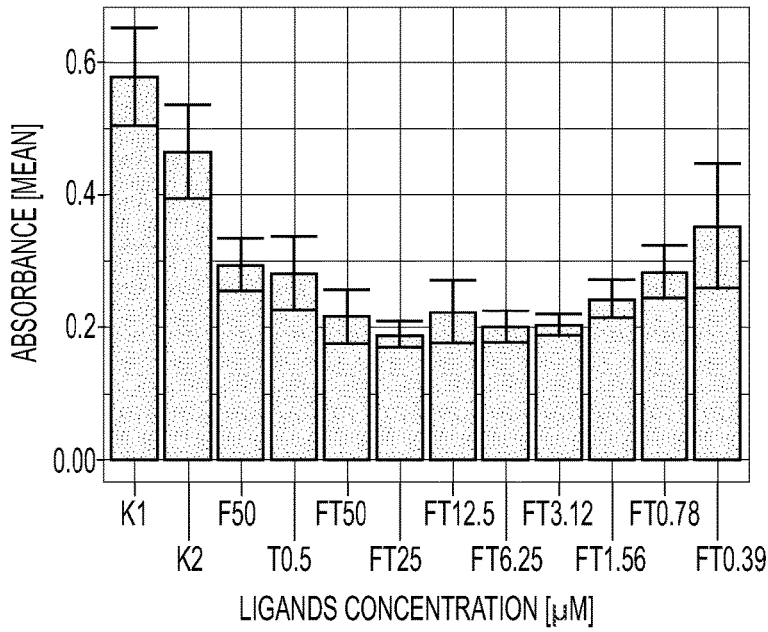

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

F - FLUVASTATIN ALONE, CONCENTRATION 50 μM

T - 0.5 μM TAXOL SYSTEM IN RPMI+10%FSC

THE DESIGNATIONS MARKED CONSECUTIVELY FROM 50 TO 0.39 DENOTE DECREASING CONCENTRATIONS OF FLUVASTATIN [μM] ADMINISTERED TOGETHER WITH TAXOL HAVING A CONSTANT CONCENTRATION OF 0.5 μM IN EACH SAMPLE IN THE SEQUENCE

ABSORBANCE [MEAN]

LIGANDS CONCENTRATION

*FIG. 5*

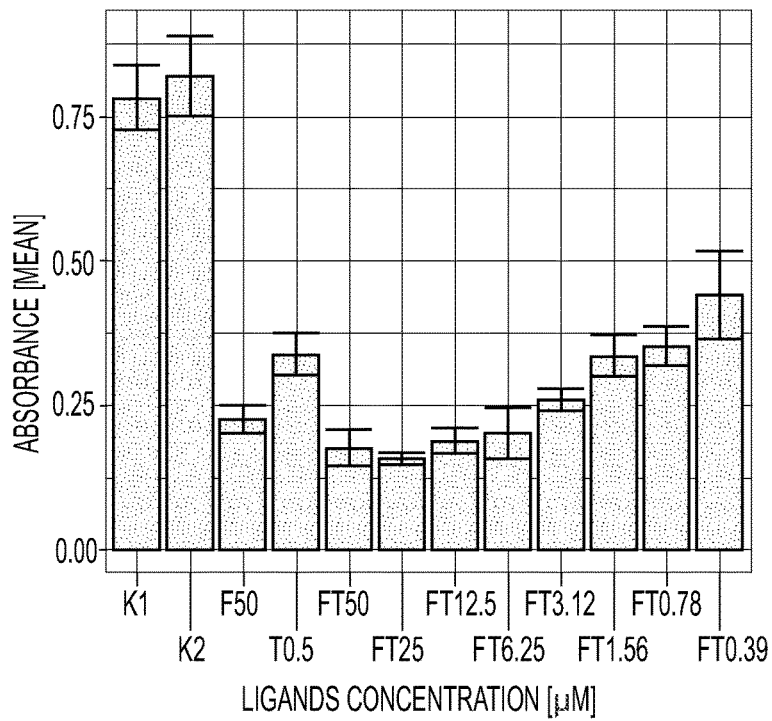

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

F - FLUVASTATIN ALONE, CONCENTRATION 50 μM

T - 0.5 μM TAXOL SYSTEM IN RPMI+10%FSC

THE DESIGNATIONS MARKED CONSECUTIVELY FROM 50 TO 0.39 DENOTE DECREASING CONCENTRATIONS OF FLUVASTATIN [μM] ADMINISTERED TOGETHER WITH TAXOL HAVING A CONSTANT CONCENTRATION OF 0.5 μM IN EACH SAMPLE IN THE SEQUENCE

ABSORBANCE [MEAN]

LIGANDS CONCENTRATION

*FIG. 6*

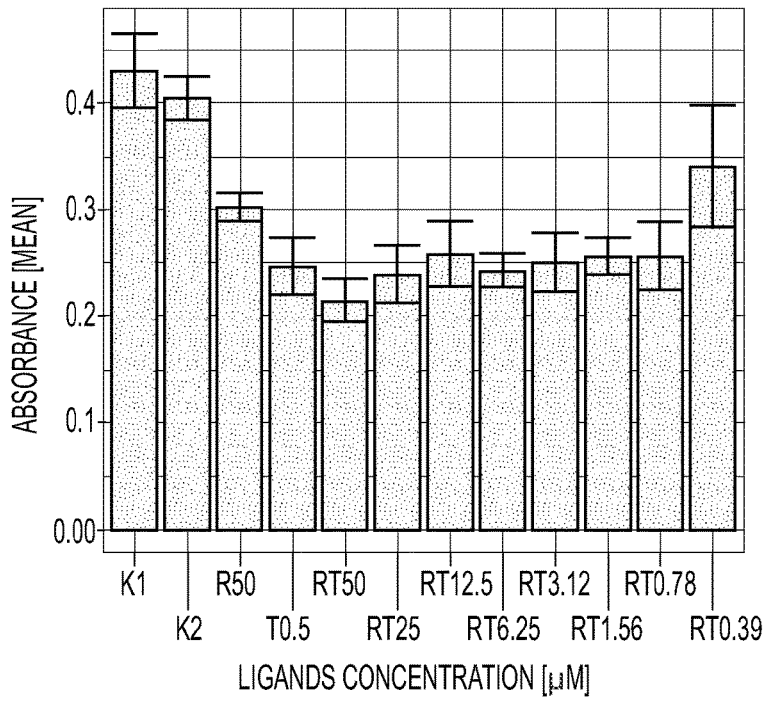

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

R - ROSUVASTATIN ALONE, CONCENTRATION 50 µM

T - 0.5 µM TAXOL SYSTEM IN RPMI+10%FSC

THE DESIGNATIONS MARKED CONSECUTIVELY FROM 50 TO 0.39 DENOTE DECREASING CONCENTRATIONS OF ROSUVASTATIN [µM] ADMINISTERED TOGETHER WITH TAXOL HAVING A CONSTANT CONCENTRATION OF 0.5 µM IN EACH SAMPLE IN THE SEQUENCE

ABSORBANCE [MEAN]

LIGANDS CONCENTRATION

*FIG. 7*

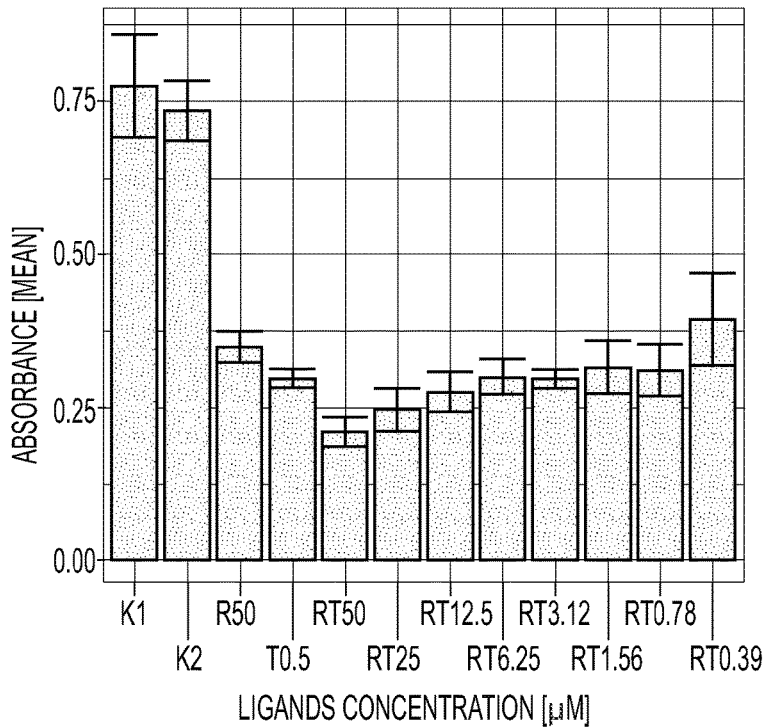

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

R - ROSUVASTATIN ALONE, CONCENTRATION 50 μM

T - 0.5 μM TAXOL SYSTEM IN RPMI+10%FSC

THE DESIGNATIONS MARKED CONSECUTIVELY FROM 50 TO 0.39 DENOTE DECREASING CONCENTRATIONS OF ROSUVASTATIN [μM] ADMINISTERED TOGETHER WITH TAXOL HAVING A CONSTANT CONCENTRATION OF 0.5 μM IN EACH SAMPLE IN THE SEQUENCE

ABSORBANCE [MEAN]

LIGANDS CONCENTRATION

*FIG. 8*

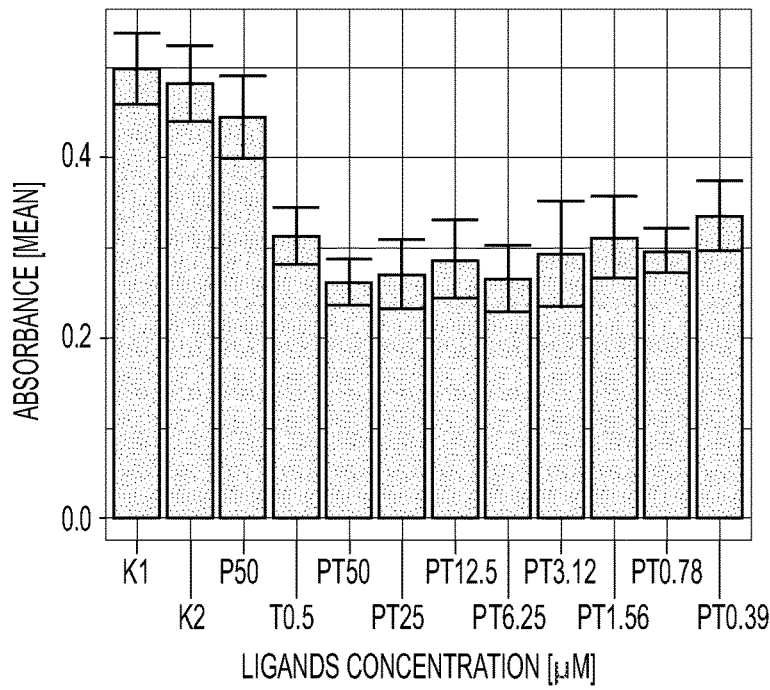

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

P - PRAVASTATIN ALONE, CONCENTRATION 50 μM

T - 0.5 μM TAXOL SYSTEM IN RPMI+10%FSC

THE DESIGNATIONS MARKED CONSECUTIVELY FROM 50 TO 0.39 DENOTE DECREASING CONCENTRATIONS OF PRAVASTATIN [μM] ADMINISTERED TOGETHER WITH TAXOL HAVING A CONSTANT CONCENTRATION OF 0.5 μM IN EACH SAMPLE IN THE SEQUENCE

ABSORBANCE [MEAN]

LIGANDS CONCENTRATION

*FIG. 9*

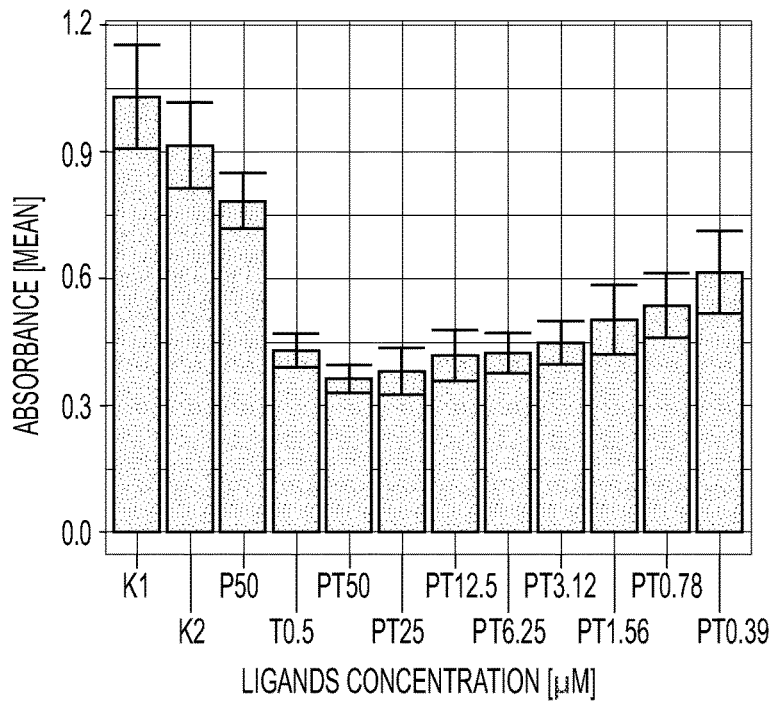

KEY:

K1 CONTROL ONLY WITH THE RPMI MEDIUM + 10% BOVINE SERUM (FSC)

K2 CONTROL ONLY WITH THE RPMI MEDIUM + 10% BOVINE SERUM (FSC)+DMSO

P - PRAVASTATIN ALONE, CONCENTRATION 50 μM

T - 0.5 μM TAXOL SYSTEM IN RPMI+10%FSC

THE DESIGNATIONS MARKED CONSECUTIVELY FROM 50 TO 0.39 DENOTE DECREASING CONCENTRATIONS OF PRAVASTATIN [μM] ADMINISTERED TOGETHER WITH TAXOL HAVING A CONSTANT CONCENTRATION OF 0.5 μM IN EACH SAMPLE IN THE SEQUENCE

ABSORBANCE [MEAN]

LIGANDS CONCENTRATION

FIG. 10

METHOD FOR THE TREATMENT OF HUMAN MELANOMA

The invention relates to a pharmaceutical composition intended for use in treatment or prevention of human melanoma.

Malignant melanoma (melanoma malignum) belongs to malignant neoplasms having the highest dynamics of incidence increase in Poland. In spite of the fact that detection of melanoma in early stadium and its curability using surgical methods (in the case of skin melanoma, cure rate by surgery exceeds 90%) are possible, initial progression of this neoplasm in Poland is still much higher than in Western European countries. Unfortunately, it translates into a low percentage of total healing in the country, on the level of merely 60-70%. Additionally, approx. 10-20% of patients suffering from melanomas have a clinical problem consisting in local recurrence and in-transit metastases, between the primary focus and a regional lymph drainage. In this group of patients, the prognosis is close to that of the group with clinical metastases to lymph nodes with a ten-year survival amounting to 20-30% only.

At present, in the systemic treatment of metastatic melanoma, the patients can take advantage of standard methods:

1) chemotherapy using single drugs (dacarbazine, temozolomide, nitrosourea derivatives, platinum compounds, taxanes, dye alkaloids, etc.);
2) chemotherapy using multi-drug programs (PC, CDBT, BOLD; CVD, etc.);
3) immunotherapy using cytokines (interferon alpha 2b, interleukin-2);
4) immunotherapy using anti-CTLA4 monoclonal antibodies (ipilimumab);
5) biochemotherapy, which consists in combining chemotherapy with immunotherapy.

Taxanes are diterpenes used in pharmaceutics, mainly as cytostatic drugs. Examples of antitumour drugs belonging to the family of taxanes include paclitaxel also known as Taxol, and docetaxel (Taxotere). Paclitaxel is a diterpene containing more than 20 chiral carbon atoms. Paclitaxel was identified in 1960 as a result of a program for searching active compounds of plant origin, realised by the U.S. National Cancer Institute, which included 35 thousand plant species, as a component of bark extract from yew *Taxus brevifolia*, having interesting antitumour activity. In 1969, the active component of the extract was isolated, and in 1971, the paclitaxel structure was determined (Eric K. Rowinsky et al., J. National Can. Inst., 82, 11247 (1990)).

As opposed to other compounds such as colchicines and vinca alkaloids, having antitumour action based on degradation of microtubules, paclitaxel exhibits a different mechanism of action, i.e. it accelerates agglutination of microtubules and inhibits degradation of tubulin (P. B. Schiff, J. Fant and S. B. Horwitz, Nature, 277, 665 (1979)).

Paclitaxel was approved for the market by FDA as an anti-cancer drug in 1993, with an indication for use in chemotherapy of ovarian cancer, breast cancer, prostate cancer, lung cancer, leukaemia, and melanoma, being particularly effective in treatment of ovarian cancer, breast cancer, and lung cancer, with efficiencies of 30%, 50%, and 20%, respectively (David, G., et al., J. Nat. Prod., 53, (1990)).

Also docetaxel accelerates aggregation of microtubules and inhibits degradation of tubulin, thereby stopping mitosis in the M phase and hindering cell division (Katzung's Pharmacology, 9th Edition (2004)). Docetaxel was considered a new-generation cytostatic drug and proved to be particularly effective in treatment of lung cancer and breast cancer (Piccart, M., Anticancer Drugs, 1995, Suppl 4:7-11). Heretofore, many other taxanes and derivatives thereof, which may find applications in treating neoplasms, were described, as well as methods for their preparation (e.g. WO94/14787, U.S. Pat. Nos. 6,916,942, 6,750,246, 6,610,860, 6,476,242, 6,369,244, 6,353,120, 6,248,908, 6,017,935, 5,977,386, 5,902,822, 5,840,929, 5,773,464, 5,773,629, 4,814,470, 4,857,653, 4,876,399, 4,942,184, 4,960,790, 5,278,324, 5,283,253, 5,352,806).

Rapid acquiring of resistance to cytostatic drugs by the malignant cells is a significant problem in therapy using conventional chemotherapeutic agents. Melanomas are particularly invulnerable to cytostatic drugs in that respect, because of expression of multiple proteins exhibiting an ability to remove cytostatics from malignant cells. These are the ABC transporters.

The family of the protein ABC transporters (ATP-Binding Cassette Transporters) occurs commonly in the animal world, from Procariota to *Homo sapiens*. It includes membrane proteins participating in transport of many substances (mainly hydrophobic) through the intra- and extracellular membranes, using energy originating from ATP hydrolysis. Their most important function is detoxication and protection of the organism from toxins. These protective functions lead to a phenomenon of multidrug resistance (MDR), by an active removal of cytostatic drugs (and other drugs) from malignant cells, which precludes reaching a proper concentration of the compounds in the tissues being treated. At present, intensive research on development of new therapies, taking into account the MDR phenomenon, is carried out. ABCG2 protein, contributing into the emergence of MDR, is present in many types of neoplasms. Its numerous substrates include taxanes. An increased activity or expression of ABCG2 may limit the effectivity of therapies using taxanes significantly.

Due to the problems described above, there is still a need for improved preparations, particularly those based on active substances already used in oncology, able to cure melanoma with humans more effectively.

The invention relates to a pharmaceutical composition comprising an aqueous solution of a taxane and an aqueous solution of a hydrophobic statin for use in treatment or prevention of human melanoma, wherein the hydrophobic statin has been selected preferably from a group including: simvastatin, atorvastatin, fluvastatin, rosuvastatin, cerivastatin, lovastatin, pitavastatin, and mixtures thereof, particularly from a group including: simvastatin, atorvastatin, fluvastatin, rosuvastatin, and mixtures thereof.

Preferably, the composition for use according to the invention comprises an aqueous solution of a taxane and an aqueous solution of simvastatin.

Preferably, the taxane is paclitaxel or docetaxel, preferably paclitaxel.

Preferably, the taxane and simvastatin are comprised in the same aqueous solution.

Preferably, the taxane and simvastatin are comprised in separate aqueous solutions.

Preferably, the composition according to the invention is additionally intended for use in treatment or prevention of embolic-thrombotic complications and palliation of symptoms connected with a neoplastic disease.

Preferably, the composition according to the invention consists of an aqueous solution of a taxane and an aqueous solution of simvastatin.

Preferably, the composition for use according to the invention constitutes an aqueous solution comprising simvastatin and a mixture of cytostatic drugs including a taxane, particularly preferably, the mixture of cytostatic drugs consisting of a taxane, cisplatin and melphalan.

In accordance with the invention, the "hydrophobic statin" is a statin having the log P coefficient determined for the water/n-octanol higher than 1, preferably higher than 3.

The partition coefficient (P) is a parameter defined as a ratio of steady-state concentrations of a substance in two immiscible solvents. In the case of the invention the first solvent is water, and the second solvent is n-octanol. The partition coefficient (P) is expressed by a ratio of two concentrations of a dissolved substance: P=Cokt/Cw, where: Cokt (mol/L) is molar concentration of the substance in octanol, while Cw (mol/L) is molar concentration of the substance in water. The measurement of P is carried out at 25° C., with the concentration of the tested substance not higher than 0.01 mol/L. If a major part of molecules of the chemical compound being tested is found in the octanol phase in such a system, the compound is hydrophobic. Otherwise, if the majority of the molecules remains in aqueous phase, it is a hydrophilic compounds. The octanol-water partition coefficient measured for various chemical compounds ranges very broadly, from 0.01 for high-polarity compounds to $10^{10}$ for highly hydrophobic substances. Therefore, its value is often reported in a logarithmic form, calculated according to the following formula: log P=log Cokt−log Cw; where: Cokt (mol/L) is molar concentration of the substance in octanol, while Cw (mol/L) is molar concentration of the substance in water.

A surprising technical effect achieved thanks to use of the invention consists in obtaining an enhancement of antitumour activity of taxane, particularly Taxol, administered in the form of an aqueous solution. The enhancement was obtained due to the presence of a hydrophobic statin, particularly simvastatin, the synergistic effect being observed toward human melanoma cells.

Surprisingly, the synergy obtained in accordance with the invention has been observed for Taxol administered in the form of a solution only in the case human melanoma cell line, and it does not occur in the case of other lines of human neoplasms, and even in the case of murine melanoma (comp. Kretzer et al., International Journal of Nanomedicine 2016: 11 885-904). While using the composition according to the invention, human malignant melanoma does not acquire resistance to taxanes, and the taxane administered accumulates selectively in the neoplastic cells till their death.

The composition for use according to the invention is a new antitumour drug effectively limiting cell division of melanoma, irrespectively of its progression phase (radial or metastatic). In a synergistic way, they cause apoptosis in the melanoma cells, with participation of mitotic catastrophe, and the effect depends on the dose of the hydrophobic statin.

The hydrophobic statin may be administered with taxanes only or within the framework of a multidrug treatment regimen, including a taxane solution, particularly in combination with cisplatin and melphalan. It allows to reduce the effective doses of taxanes used in the presence simvastatin.

Simultaneously, the use of the invention eliminates the necessity to use a low-efficiency cisplatin-Taxol combination or other treatment regimens including taxanes, to which the neoplasm becomes resistant rapidly.

It was observed also that the combination of a taxane and a hydrophobic statin, particularly simvastatin, does not affect healthy (non-malignant) human fibroblasts. It is also poorly efficient in treatment of other neoplasms, not originating from the ectoderm, particularly colorectal carcinoma. In the case of melanoma, embolic-thrombotic diseases are a frequent complication in the treatment, even with new medicinal preparations (e.g., antibodies). Statins, which affect the inhibition of activity of the coagulation system and the delay of the clot formation in blood vessels, reduce the expression of tissular thromboplastin and thrombin production, inhibit the platelet aggregation and activation, should enhance the treatment effects additionally. Therefore, irrespective of the enhanced antitumour activity toward human melanoma, due to the action of a hydrophobic statin, the composition according to the invention is suitable for use in treatment of embolic-thrombotic complications which accompany this neoplasm, and in palliation of symptoms connected with the neoplastic disease. The administered doses of the statin should be adapted by a person skill in the art to the dose of the taxane and general condition of the patient. A possibility to reach high doses of statins (up to approx. 25-30 mg/kg/day), corresponding to in-vitro antiproliferative concentrations, was confirmed [van der Spek, Holstein], however with a general toxicity level still accepted clinically.

In a preferable embodiment, the composition according to the invention is a drug against the human melanoma, intended to be administered as an infusion, in the form of a binary system of a taxane together with a hydrophobic statin.

In a preferable embodiment, the composition according to the invention should be administered as an infusion or in hydrophobic nanocapsules providing transport to malignant cells, e.g. of human melanoma.

BRIEF DESCRIPTION OF THE DRAWINGS

FIGS. 1A to 1C: The results of the tests of the effect of Taxol-simvastatin composition on the prolliferation of A357P, WM35 (radial phase) and WM239A cell lines, obtained in the "crystal violet" assay, in comparision to that of pure Taxol, FIG. 3: The "crystal violet" assay of the effect of simvastatin-Taxol on the proliferation of the colorectal carcinoma HT-29 cells obtained in the "crystal violet" assay, FIG. 4: The results of the tests of the effect of atorvastatin-Taxol combination on the proliferation of melanoma cells of the A345P line (malignant line) obtained in the "crystal violet" assay.

FIG. 5: The results of the tests of the effect of fluvastatin-Taxol combination on the proliferation of cells from the WM239A line (metastatic line) obtained in the "crystal violet" assay.

FIG. 6: The results of the tests of the effect of fluvastatin-Taxol combination on the proliferation of melanoma cells of the A375P line (malignant line) obtained in the "crystal violet" assay.

FIG. 7: The results of the tests of the effect of rosuvastatin-Taxol combination on the proliferation of cells from the WM239A line (metastatic line) obtained in the "crystal violet" assay.

FIG. 8: The results of the tests of the effect of rosuvastatin-Taxol combination on the proliferation of melanoma cells of the A375P line (malignant line) obtained in the "crystal violet" assay.

FIG. 9: The results of the tests of the effect of pravastatin-Taxol combination on the proliferation of cells from the WM239A line (metastatic line) obtained in the "crystal violet" assay FIG. 10: The results of the tests of the effect of pravastatin-Taxol combination on the proliferation of melanoma cells of the A375P line (malignant line) obtained in the "crystal violet" assay.

Figure 2:
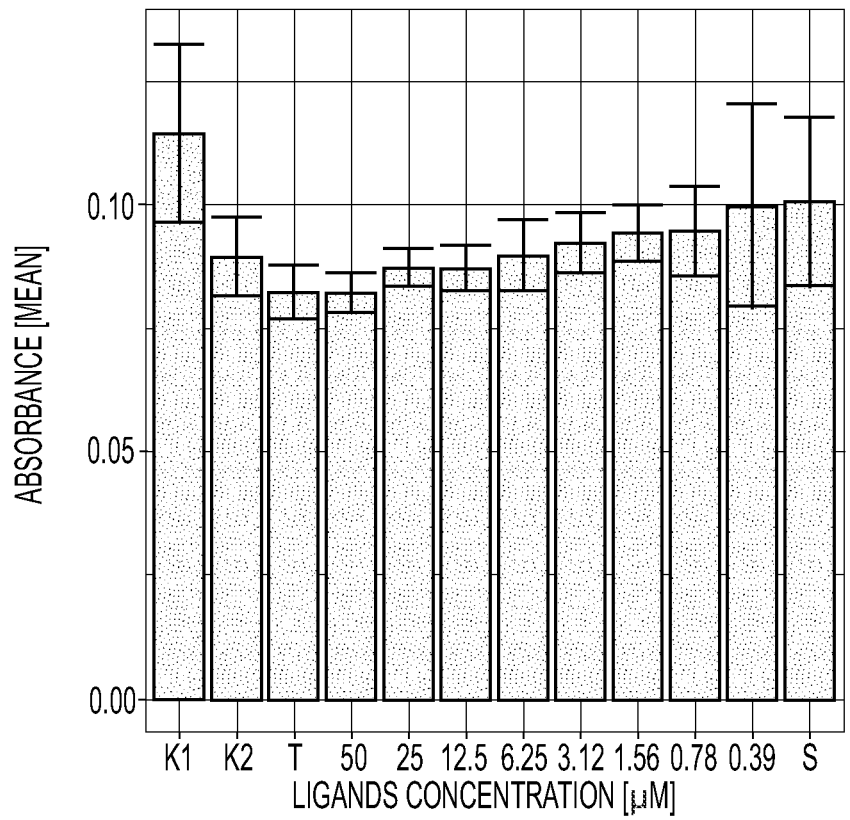
FIG. 2: results of action of a simvastatin-Taxol composition of the proliferation of cells from the S91 cell line, obtained in the "crystal violet" assay.

Below, exemplary embodiments of the invention are discussed.

EXAMPLE 1. EFFECT OF SIMVASTATIN ADMINISTERED TOGETHER WITH TAXOL ON THE PROLIFERATION OF HUMAN MELANOMA CELLS (MELANOMA MALIGNUM)

The goal of the analysis was to evaluate, whether the administration of simvastatin in a combination with Taxol (or a treatment regimen including Taxol) may block synergistically the divisions of human melanoma cells. The tests were carried out using cell lines of human melanoma originating from three stages of development: WM35 of the radial growth phase, WM239A metastatic line and A375P metastasis to lungs, malignant line. The proliferation tests were carried out by the "crystal violet" assay and the MTT assay.

"Crystal Violet" Assay

The "crystal violet" assay (see: Gillies R J, Didier N, Denton M (1986) Determination of cell number in monolayer cultures, Anal Biochem 159: 109-113) is based on an assumption that the living cells undergo dyeing while remaining attached to the substrate, while the dead cells are being removed together with the culture medium. Absorbance of the solution measured at the wavelength of 540 inn is proportional to the amount of the dyed cells [Gillies R J et al., 1986]. The test has a relatively high sensitivity and accuracy.

The cells were sown on a 96-well plate in the amount of $1.5 \times 10^3$ per well. After growing the cells with proper ligands, the supernatant liquid from above the cells was removed and the cells were washed with 200 µl of the PBS buffer solution with a temperature of 37° C. Then, the PBS was decanted, 200 µl of methanol were added to every well and the samples were incubated for 15 minutes at a temperature of 20° C. Methanol was removed from above the cells and after drying the plate, 150 µl of 5% of crystal violet solution in 20% aqueous methanol solution were added to every well. After 2 minutes, the dye was decanted, the cells were washed thrice with water, and then, a decolorant (sodium citrate/citric acid buffer in 50% aqueous methanol) was added in the amount of 200 µl per well. After 30 min, the absorbance of the solution at the wavelength of 540 nm was measured vs. a blank.

MTT Assay

The MTT assay is based on the activity of an enzyme (mitochondrial dehydrogenase) for transformation of orange-yellow water-soluble tetrazol salt (3-(4,5-dimethyl-thiazol-2-yl)-2,5-diphenyltetrazolium bromide) to the form of a insoluble formazan, a product of the aforementioned reaction having purple colour. After dissolving the formazan crystals in acidic isopropanol, a solution forms, which colour intensity is measured spectrophotometrically at 570 inn. The amount of coloured reduced MTT is directly proportional to the oxidative activity of the mitochondria in the cell, and under strictly defined experimental conditions—to the number of metabolically active (or live) cells in a given population. Also, the MTT assay may be used for both proliferation of cells and viability in cell populations which stopped dividing, but are metabolically active. Thus, the MTT assay is currently used for evaluation of cytotoxic activity, and it is recommended as a reference by international standard-setting organisations.

The cells were sown on a 96-well plate in the amount of $1.5 \times 10^3$ per well. After growing the cells with proper ligands, the supernatant liquid from above the cells was removed and the cells were washed with 200 µl of the PBS buffer solution with a temperature of 37° C. Then, the liquid with the ligands was removed from above the cells, and the cells were washed with 200 µl of RPMI medium without serum at a temperature of 37° C. Then, the medium was decanted and a solution of MTT in the RPMI medium was added, with a final concentration of MTT in a well amounting to 0.5 mg/ml, and 150 µl of the dye solution per well were added. The plate was incubated at 37° C. with 5% of $CO_2$ for 3 h. After the incubation, the liquid was removed from above the cells, and 150 µl of acidified (HCl) isopropanol per well were added; then, the plate was shaken for 20 mm in a horizontal shaker. Absorbance was measured at the wavelength of 570 nm (Synergy HT Bio-tek spectrometer).

The results of the tests of the effect of Taxol-simvastatin composition on the proliferation of A375P, WM35 (radial phase) and WM239A cell lines, obtained in the "crystal violet" assay, in comparison to that of pure Taxol, are shown in FIGS. 1A-C, respectively. The obtained results were statistically significant (Table 1).

TABLE 1

Statistical analysis of the results obtained in the "crystal violet" assay.

| A375P | | WM35 | | WM239A | |
| --- | --- | --- | --- | --- | --- |
| tests | Value of p | tests | Value of p | tests | Value of p |
| S vs. K | 1.67e−07 | S vs. K | 1.10e−07 | S vs. K | 6.39e−15 |
| S vs. 25 | 7.91e−14 | S vs. 25 | 5.13e−13 | S vs. 25 | 5.21e−09 |
| S vs. 12.5 | 6.10e−11 | S vs. 12.5 | 2.22e−12 | S vs. 12.5 | 2.26e−07 |
| T vs. K | 1.94e−07 | T vs. K | 1.02e−07 | T vs. K | 1.62e−11 |
| K vs. z50 | 6.21e−09 | K vs. z50 | 9.50e−09 | K vs. z50 | 1.11e−13 |
| K vs. 25 | 3.66e−09 | K vs. 25 | 1.68e−09 | K vs. 25 | 1.72e−15 |
| K vs. 12.5 | 1.91e−08 | K vs. 12.5 | 8.41e−09 | K vs. 12.5 | 8.15e−15 |
| K vs. 6.25 | 4.79e−08 | K vs. 6.25 | 3.45e−09 | K vs. 6.25 | 1.15e−14 |
| K vs. 3.12 | 5.28e−08 | K vs. 3.12 | 5.15e−09 | K vs. 3.12 | 3.45e−16 |
| K vs. 1.56 | 3.28e−09 | K vs. 1.56 | 6.88e−09 | K vs. 1.56 | 1.26e−13 |
| K vs. 0.78 | 1.48e−08 | K vs. 0.78 | 2.44e−10 | K vs. 0.78 | 9.64e−12 |
| K vs. 0.39 | 2.05e−08 | K vs. 0.39 | 8.38e−11 | K vs. 0.39 | 2.43e−15 |
| T vs. z50 | 1.86e−11 | T vs. z50 | 1.10e−07 | T vs. z50 | 4.04e−18 |
| T vs. 25 | 5.37e−13 | T vs. 25 | 5.13e−13 | T vs. 25 | 1.15e−09 |
| T vs. 12.5 | 3.17e−10 | T vs. 12.5 | 2.22e−12 | T vs. 12.5 | 7.68e−09 |
| T vs. 6.25 | 7.99e−09 | T vs. 6.25 | 1.02e−07 | T vs. 6.25 | 1.18e−14 |
| T vs. 3.12 | 8.04e−07 | T vs. 3.12 | 9.50e−09 | T vs. 3.12 | 5.95e−11 |
| T vs. 1.56 | 0.019 | T vs. 1.56 | 1.68e−09 | T vs. 1.56 | 1.29e−12 |
| T vs. 0.78 | 0.010 | T vs. 0.78 | 8.41e−09 | T vs. 0.78 | 1.28e−12 |
| T vs. 0.39 | 0.013 | T vs. 0.39 | 3.45e−09 | T vs. 0.39 | 2.13e−09 |

The proliferation tests carried out using three cell lines of human melanoma by the "crystal violet" assay prove that simvastatin inhibits permanently the proliferation of various lines of human melanoma cells synergistically, and depending on the dose (e.g., from 50 to 12.5 µM) in connection with the taxoid used (e.g., Taxol with a constant concentration of 0.5 µM). Probably, the presence of simvastatin supports the selective accumulation of Taxol in the melanoma cells, realised by suppression of drug resistance to Taxol of human melanoma cells as a result of simvastatin action. The therapeutically effective range of the applied doses of simvastatin is comprised in the range of 12.5 to 50 µM, giving a synergistic effect with the applied Taxol having a concentration of 0.5 µM.

The result was confirmed also by the MTT assay for all three melanoma cell lines originating from three stages of development (WM35 of the radial growth phase, WM239A metastatic line and A375P metastasis to lungs, malignant line).

EXAMPLE 2. EFFECT OF SIMVASTATIN ADMINISTERED TOGETHER WITH TAXOL AND OTHER CYTOSTATIC DRUGS ON THE TAXOID TOXICITY AGAINST HUMAN MELANOMA CELLS (MELANOMA MALIGNUM)

Toxicities of the applied drugs were tested by a measurement of reduced and oxidised glutathione GSH/GSSG contents in the human melanoma cells. The glutathione contents were analysed by RP-HPLC. A method from prior art [references 1-4] was used.

The applied method consists in a reaction of GSH and GSSG with N-dinitrofluorobenzene, yielding N,S-dinitro-derivatives in the case of GSH and N,N-dinitro-derivatives in the case of GSSG. The elutions were carried out in a water-acetonitrile system, in accordance to the increasing acetonitrile concentration.

Determination of the levels of reduced glutathione, oxidised glutathione, and total glutathione were carried out using an RP-HPLC system from Shimadzu (SPD-M10VP photodiode matrix detector, class VP 7.2 software). The separations were carried out at a temperature of 20° C. using a Luna 5u C18 (Z) column (250 mm×4.6 mm, from Phenomenex), with a guard column with the same packing. Grade solvents were used as the eluant in the separations: acetonitrile/0.1% TFA and H$_2$O/0.1% TFA. The separation was obtained in gradient elution, under a non-linear increase in the acetonitrile concentration from 20% to 100% during 90 minutes, at a flow of 1.0 ml/min. Samples with a volume of 20 μl were introduced into the column, filtered earlier using PTFE filters with a pore diameter of 0.2 μm (Supelco). The analysis of the compounds was carried out with UV-VIS detection at 365 nm. The cells were suspended in a 70% PCA/1 mM BPDS/0.9% NaCl solution in a 1:3 ratio, sonicated for 3×5 seconds (Bandelin SonoplusGM70) at a temperature of 4° C. and centrifuged under 1400 g at a temperature of 4° C. for 10 minutes. The prepared supernatant was used for the assays.

For identification of the tested compounds, proper standard solutions were used: GSH and GSSG.

All standard solutions were prepared in 10% PCA/1 mM BPDS, in redistilled water.

To determine the GSH and GSSG levels, calibration curves were used, prepared for standard solutions in the concentration range of 13 to 75 nmol/ml of the corresponding cell homogenate. The incubation mixture contained, respectively: supernatant originating from the cells, N-methyl-L-lysine (internal standard), 10% PCA/1 mM BPDS, 2 M KOH-2.4 M KHCO$_3$ and 1% DNFB.

In the case of the calibration curve, the incubation mixture was prepared in an analogous way, but various volumes of standard solutions were added, and the final volume was controlled by the amount of the 10% PCA/1 mM BPDS added. After 24 h derivatization at room temperature, in darkness, the samples were acidified by adding 70% PCA and centrifuged for 2 minutes under 5600 g. The obtained supernatant was filtered through a PTFE-Supelco filter, introduced into the column, and 90-minute separation of the analysed compounds was carried out. The chromatograms were worked out identifying the compounds being separated according to their retention times, based on the standards available, and totalising the surface areas of the chromatographic peaks in the ranges of selected retention times.

TABLE 2

| Cell line + added pharmaceuticals | Initial cell count 0 h [mln] | Cell count after 48 h [mln] | GSH nmol/million of cells | GSSG nmol/million of cells | Total glutathione nmol/million of cells | GSH/GSSG |
|---|---|---|---|---|---|---|
| A375P K | 3.8 | 6.4 | 0.08 | 0.85 | 1.8 | 0.095 |
| A375P TCM | 3.8 | 5.3 | 0.35 | 2.29 | 4.9 | 0.154 |
| A375P TCM + S | 3.8 | 3.1 | 0.5 | 2.5 | 5.4 | 0.202 |
| WM239A K | 4 | 6.6 | 0.12 | 1.36 | 2.8 | 0.09 |
| WM239A TCM | 4 | 4.6 | 0.35 | 1.67 | 3.7 | 0.21 |
| WM239A TCM + S | 4 | 3.3 | 0.50 | 2.01 | 4.5 | 0.25 |
| WM35 K | 5.3 | 6.1 | 0.39 | 0.82 | 2.0 | 0.48 |
| WM35 TCM | 5.3 | 4.9 | 1.04 | 1.92 | 4.9 | 0.54 |
| WM35 TCM + S | 5.3 | 3.5 | 1.21 | 1.95 | 5.1 | 0.62 |

Key:
K—control,
TCM—Taxol, cisplatin, melphalan [0.5 μM],
TCM + S—TCM + simvastatin [5 μM].
The obtained results confirm the synergism observed in Example 1.

EXAMPLE 3. SIMVASTATIN SELECTIVELY INCREASES THE TAXANES TAKE-UP INTO HUMAN MELANOMA CELLS

The goal of the analysis was to evaluate, whether the administration of simvastatin in a combination with Taxol may increases selectively the Taxol concentration in malignant cells. A method using the HPLC technique was developed.

The tests were carried out using cell lines of human melanoma originating from three stages of development: WM35 of the radial growth phase, WM239A metastatic line and A375P metastasis to lungs, malignant line. For every measuring point, cells were grown in 4 100 mm coming dishes for each separate cell line. Analyses for the control system (cells grown in the presence of 10% FSC serum in the RPMI medium), for samples containing an addition of 0.5 μM taxane, and for those containing an addition of SIMTAX composition (0.5 μM taxane+20 μM simvastatin) were carried out. The analyses were repeated thrice in independent experiments, obtaining similar results. The results were averaged and reported in µM per a million of cells. The cells were counted using a Countess Invitrogen™ counter.

For determination of the amount of drug absorbed by the melanoma cells, chromatographic method was used. An HPLC system (Shimadzu Corporation Japan) consisting of two LC 10AT vp high-pressure pumps, a DGU-14A degasser, a CTO-10 ASvp oven for the column thermostating, an SIL-10 ADvp automatic sample feeder, and an SPD-M10 Avp diode detector, was used for the measurements. CLASS-VP 7.2.1 software was used.

Description of the Method

The samples were separated on a Phenomenex Gemini -Nx 5µ $C_{18}$ (4.6×150 mm i.d) column+guard column from Phenomenex (4×3 mm i.d.) with identical packing, at a temperature of 20° C. Eluant with the following composition: solvent A (water+0.1% trifluoroacetic acid [TFA]) and solvent B (acetonitrile 0.1% TFA) was used. The sample was separated in the following gradient system: 20% of solvent B to 30% of solvent B linearly for 15 min, next linearly to 34% for 6 min, linearly to 100% of solvent B for 24 min consecutively, then 10 min isocratically at 100% of solvent B. The column was recalibrated for 15 mm in 20% of solvent B. 20-µl samples were introduced at a flowrate of 1.0 ml/min during 65 min with a UV-Vis detection at 220 nm.

The results were validated in two steps, by comparing the obtained Rt values to Rt values of standards, and by analysis of spectra of the separated compound and their comparison with spectra of the standards.

Procedure for Recovery of the Drug from the Tissue

A frozen dry pellet was flushed with 650 µl of a solution (2/1 isopropanol, methanol+10% acetonitrile), then sonicated 3×15 s and frozen for 24 h. After thawing, the sample was shaken lightly for 30 min, 200 µl of physiological saline and 1083 µl of chloroform were added, stirring vigorously for 3×4 min. Separation of the organic phase from the aqueous phase was carried out by centrifugation at 10,000 revolutions/10 min. The collected chloroform phase were subjected to concentration under partial vacuum in a concentrator at 4° C., and to second drying under argon atmosphere. The precipitate was dissolved in 100 µl of methanol and separated by HPLC.

Recovery

99% recovery in relation to standards suspended in physiological saline was obtained.

Measurement error does not exceed 5% for both compounds in the above method.

Conclusion: Simvastatin selectively increases the taxanes take-up into human melanoma cells irrespective of the progression phase, from which a given kind of cells originates. Simvastatin increases the Taxol content in the human melanoma cells by two hundred percent on average in relation to the control with Taxol alone. Taxol retention is a permanent process.

EXAMPLE 4. EFFECT OF OTHER STATINS ADMINISTERED TOGETHER WITH TAXOL ON THE PROLIFERATION AND TOXICITY OF HUMAN MELANOMA CELLS (MELANOMA MALIGNUM)

The goal of the analysis was to evaluate, whether the administration of other statins with hydrophobicity approximate to that of simvastatin in a combination with Taxol (docetaxel) may block synergistically the divisions of human melanoma cells. The following statins were used in the studies: atorvastatin, fluvastatin, rosuvastatin, and pravastatin. The tests were carried out using cell lines of human melanoma originating from invasive stages of development: WM239A metastatic line and A375P P-metastasis to lungs, malignant line. The proliferation/cytotoxicity tests were carried out by the "crystal violet" assay and the MTT assay. Methodology according to that described in Example 1 was used. Additionally, the toxicity was analysed by investigations of reduced and oxidised glutathione contents. HPLC method was used.

The results of the tests of the effect of atorvastatin-Taxol combination on the proliferation of cells from the WM239A line (metastatic line) obtained in the "crystal violet" assay are shown in Table 4 below and in FIG. 3.

TABLE 4

Statistical analysis of the results obtained in the "ciystal violet" assay for the WM239A line and atorvastatin-Taxol combination.

| Dilution of atorvastatin [µM] vs. Control | Value of p |
|---|---|
| 50 vs. K | 1.10e-09 |
| 0.5 vs. K | 1.45e-08 |
| 50 vs. K | 6.40e-10 |
| 25 vs. K | 1.70e-09 |
| 12.5 vs. K | 4.37e-10 |
| 6.25 vs. K | 7.01e-09 |

TABLE 3

Analysis of Taxol take-up into human melanoma cells

| | Line name and cell count [mln] | | | | | | | | |
|---|---|---|---|---|---|---|---|---|---|
| | WM 35 13.2 | | | WM239A 15.6 | | | A375P 16.1 | | |
| variables | Integral of the peak surface area | Taxol concentration [µM]/million of cells | % content in cells | Integral of the peak surface area | Taxol concentration [µM]/million of cells | % content in cells | Integral of the peak surface area | Taxol concentration [µM]/ million of cells | % content in cells |
| control | 0 | 0 | 0 | 0 | 0 | 0 | 0 | 0 | 0 |
| TCM | 402994 | 23.83/1.805 | 100 | 619558 | 36.8/2.36 | 100 | 318221 | 18.9/1.17 | 100 |
| TCM + simvastatin | 631422 | 37.5/2.84 | 156 | 1237116 | 73.48/4.71 | 199 | 631547 | 37.5/2.32 | 198 |

TABLE 4-continued

Statistical analysis of the results obtained in the "ciystal violet"
assay for the WM239A line and atorvastatin-Taxol combination.

| Dilution of atorvastatin [μM] vs. Control | Value of p |
|---|---|
| 3.12 vs. K | 1.15e−08 |
| 1.56 vs. K | 8.90e−09 |
| 0.78 vs. K | 7.46e−07 |
| 0.39 vs. K | 1.71e−07 |

The results of the tests of the effect of atorvastatin-Taxol combination on the proliferation of melanoma cells of the A375P line (malignant line) obtained in the "crystal violet" assay are shown in Table 5 below and in FIG. 4.

TABLE 5

Statistical analysis of the results obtained in the "crystal violet"
assay for the A375P line and atorvastatin-Taxol combination.

| Dilution of atorvastatin [μM] vs. Control | Value of p |
|---|---|
| 50 vs. K | 4.81e−08 |
| 0.5 vs. K | 1.36e−07 |
| 50 vs. K | 2.93e−08 |
| 25 vs. K | 3.88e−08 |
| 12.5 vs. K | 2.77e−08 |
| 6.25 vs. K | 1.00e−07 |
| 3.12 vs. K | 2.35e−08 |
| 1.56 vs. K | 5.22e−08 |
| 0.78 vs. K | 2.84e−08 |
| 0.39 vs. K | 5.63e−08 |

The results of the tests of the effect of fluvastatin-Taxol combination on the proliferation of cells from the WM239A line (metastatic line) obtained in the "crystal violet" assay are shown in Table 6 below and in FIG. 5.

TABLE 6

Statistical analysis of the results obtained in the "crystal violet"
assay for the WM239A line and fluvastatin-Taxol combination.

| Dilution of fluvastatin [μM] vs. Control | Value of p |
|---|---|
| 50 vs. K | 1.10e−09 |
| 0.5 vs. K | 1.45e−08 |
| 50 vs. K | 6.40e−10 |
| 25 vs. K | 1.70e−09 |
| 12.5 vs. K | 4.37e−10 |
| 6.25 vs. K | 7.01e−09 |
| 3.12 vs. K | 1.15e−08 |
| 1.56 vs. K | 8.90e−09 |
| 0.78 vs. K | 7.46e−07 |
| 0.39 vs. K | 1.71e−07 |

The results of the tests of the effect of fluvastatin-Taxol combination on the proliferation of melanoma cells of the A375P line (malignant line) obtained in the "crystal violet" assay are shown in Table 7 below and in FIG. 6.

TABLE 7

Statistical analysis of the results obtained in the "crystal violet"
assay for the A375P line and fluvastatin-Taxol combination.

| Dilution of fluvastatin [μM] vs. Control | Value of p |
|---|---|
| 50 vs. K | 3.94e−10 |
| 0.5 vs. K | 2.50e−10 |

TABLE 7-continued

Statistical analysis of the results obtained in the "crystal violet"
assay for the A375P line and fluvastatin-Taxol combination.

| Dilution of fluvastatin [μM] vs. Control | Value of p |
|---|---|
| 50 vs. K | 2.36e−11 |
| 25 vs. K | 3.62e−09 |
| 12.5 vs. K | 3.96e−10 |
| 6.25 vs. K | 3.99e−12 |
| 3.12 vs. K | 2.26e−09 |
| 1.56 vs. K | 2.42e−10 |
| 0.78 vs. K | 5.19e−10 |
| 0.39 vs. K | 1.31e−07 |

The results of the tests of the effect of rosuvastatin-Taxol combination on the proliferation of cells from the WM239A line (metastatic line) obtained in the "crystal violet" assay are shown in Table 8 below and in FIG. 7.

TABLE 8

Statistical analysis of the results obtained in the "crystal violet"
assay for the WM239A line and rosuvastatin-Taxol combination.

| Dilution of rosuvastatin [μM], K - control | Value of p |
|---|---|
| 50 vs. K | 5.18e−06 |
| 0.5 vs. K | 2.60e−08 |
| 50 vs. K | 9.67e−09 |
| 25 vs. K | 1.56e−08 |
| 12.5 vs. K | 6.69e−08 |
| 6.25 vs. K | 1.14e−07 |
| 3.12 vs. K | 3.22e−08 |
| 1.56 vs. K | 1.64e−07 |
| 0.78 vs. K | 6.69e−08 |
| 0.39 vs. K | 0.0025 |

The results of the tests of the effect of rosuvastatin-Taxol combination on the proliferation of melanoma, cells of the A375P line (malignant line) obtained in the "crystal violet" assay are shown in Table 9 below and in FIG. 8.

TABLE 9

Statistical analysis of the results obtained in the "crystal violet"
assay for the A375P line and rosuvastatin-Taxol combination.

| Dilution of rosuvastatin [μM], K - control | Value of p |
|---|---|
| 50 vs. K | 5.81e−07 |
| 0.5 vs. K | 5.26e−07 |
| 50 vs. K | 7.93e−08 |
| 25 vs. K | 4.10e−08 |
| 12.5 vs. K | 7.51e−08 |
| 6.25 vs. K | 1.71e−07 |
| 3.12 vs. K | 5.37e−07 |
| 1.56 vs. K | 5.07e−08 |
| 0.78 vs. K | 5.47e−08 |
| 0.39 vs. K | 1.83e−07 |

The results of the tests of the effect of pravastatin-Taxol combination on the proliferation of cells from the WM239A line (metastatic line) obtained in the "crystal violet" assay are shown in Table 10 below and in FIG. 9.

TABLE 10

Statistical analysis of the results obtained in the "crystal violet" assay for the WM239A line and pravastatin-Taxol combination.

| Dilution of pravastatin [μM], K - control | Value of p |
|---|---|
| 50 vs. K | 0.024 |
| 0.5 vs. K | 9.07e−08 |
| 50 vs. K | 7.25e−09 |
| 25 vs. K | 1.39e−08 |
| 12.5 vs. K | 9.35e−08 |
| 6.25 vs. K | 7.99e−09 |
| 3.12 vs. K | 2.43e−06 |
| 1.56 vs. K | 4.89e−07 |
| 0.78 vs. K | 4.93e−08 |
| 0.39 vs. K | 8.52e−07 |

The results of the tests of the effect of pravastatin-Taxol combination on the proliferation of melanoma cells of the A375P line (malignant line) obtained in the "crystal violet" assay are shown in Table 11 below and in FIG. 10.

TABLE 11

Statistical analysis of the results obtained in the "crystal violet" assay for the A375P line and pravastatin-Taxol combination.

| Dilution of pravastatin [μM], K - control | Value of p |
|---|---|
| 50 vs. K | 0.0004 |
| 0.5 vs. K | 6.11e−07 |
| 50 vs. K | 4.47e−07 |
| 25 vs. K | 1.23e−07 |
| 12.5 vs. K | 1.54e−07 |
| 6.25 vs. K | 3.93e−07 |
| 3.12 vs. K | 4.32e−07 |
| 1.56 vs. K | 2.73e−07 |
| 0.78 vs. K | 6.25e−07 |
| 0.39 vs. K | 3.82e−06 |

Conclusion: As it results from the proliferation tests carried out on cells from three lines of human melanoma by the "crystal violet" assay, atorvastatin, fluvastatin, and to a much lesser degree rosuvastatin, permanently inhibit synergistically and depending on the dose (50-12.5 μM) with the applied docetaxel regimen at a constant concentration of 0.5 μM the proliferation of human melanoma cells by selective accumulation of Taxol in the melanoma cells, realised by removal of resistance to Taxol of human melanoma cells. The therapeutically effective range of the applied doses of the tested statins is comprised in the range of 12.5 to 50 μM, giving a synergistic effect with the applied taxane having a concentration of 0.5 μM. The result was confirmed by the MTT assay for all three melanoma cell lines originating from three stages of development (WM35 of the radial growth phase, WM239A metastatic line and A375P metastasis to lungs, malignant line).

EXAMPLE 5. EFFECT OF OTHER STATINS ADMINISTERED TOGETHER WITH TAXOL AND OTHER CYTOSTATIC DRUGS ON THE TOXICITY OF THE TAXOID AGAINST HUMAN MELANOMA CELLS (MELANOMA MALIGNUM)

Toxicities of the applied drugs were tested by a measurement of GSH/GSSG contents in the human melanoma cells. The glutathione contents were analysed by HPLC. A method drawn from the papers by [Bronowicka, Wróbel, Dominik] was used, described in detail in Example 2. The obtained results are presented in Tables 12a-c below.

TABLE 12a

| Cell line + added pharmaceuticals | Initial cell count 0 h [mln] | Cell count after 48 h [mln] | GSH nmol/million of cells | GSSG nmol/million of cells | Total glutathione nmol/million of cells | GSH/GSSG |
|---|---|---|---|---|---|---|
| A375P K | 5.9 | 12.1 | 0.98 | 0.12 | 1.22 | 8.14 |
| A375P T | 5.9 | 11.1 | 0.94 | 0.14 | 1.22 | 6.78 |
| A375P T + F | 5.9 | 9.2 | 2.06 | 0.24 | 2.54 | 8.57 |
| A375P T + A | 5.9 | 8.3 | 1.39 | 0.22 | 1.84 | 6.22 |
| A375P T + P | 5.9 | 9.8 | 1.36 | 0.21 | 1.77 | 6.58 |
| A375P T + R | 5.9 | 10.1 | 1.03 | 0.13 | 1.30 | 7.70 |

TABLE 12b

| Cell line + added pharmaceuticals | Initial cell count 0 h [mln] | Cell count after 48 h [mln] | GSH nmol/million of cells | GSSG nmol/million of cells | Total glutathione nmol/million of cells | GSH/GSSG |
|---|---|---|---|---|---|---|
| WM239A K | 6.2 | 12.9 | 0.01 | 0.07 | 0.1 | 0.17 |
| WM239A T | 6.2 | 10.1 | 1.07 | 0.16 | 1.40 | 6.53 |
| WM239A T + F | 6.2 | 8.2 | 3.69 | 0.35 | 4.40 | 10.55 |
| WM239A T + A | 6.2 | 7.4 | 3.15 | 0.39 | 3.93 | 8.00 |
| WM239A T + P | 6.2 | 10.1 | 0.14 | 0.08 | 0.31 | 1.67 |
| WM239A T + R | 6.2 | 9.1 | 1.2 | 0.21 | 1.62 | 5.83 |

TABLE 12c

| Cell line + added pharmaceuticals | Initial cell count 0 h [mln] | Cell count after 48 h [mln] | GSH nmol/million of cells | GSSG nmol/million of cells | Total glutathione nmol/million of cells | GSH/GSSG |
|---|---|---|---|---|---|---|
| WM35 K | 7.1 | 11.9 | 0.29 | 0.76 | 2.1 | 0.38 |
| WM35 T | 7.1 | 10.1 | 1.12 | 1.88 | 4.8 | 0.59 |
| WM35 T + F | 7.1 | 7.3 | 1.21 | 2.11 | 4.42 | 0.57 |
| WM35 T + A | 7.1 | 6.7 | 1.15 | 2.39 | 5.4 | 0.48 |
| WM35 T + P | 7.1 | 9.7 | 1.14 | 2.08 | 3.9 | 0.54 |
| WM35 T + R | 7.1 | 8.4 | 1.21 | 2.21 | 4.5 | 0.55 |

Key:
K—control, T—Docetaxel [0.5 µM], T+A—T+atorvastatin [20 µM], T+F—T+fluvastatin [20 µM], T+P—T+pravastatin [20 µM], T+R—T+rosuvastatin [20 µM], Conclusion: Toxicity of the applied pharmaceuticals increases when administered in the form of a statin+taxane composition. A hydrophilic statin, i.e. pravastatin, is not toxic and it does not affect the malignant cells.

EXAMPLE 6. ANALYSIS OF PHARMACEUTICALS' TAKE-UP INTO HUMAN MELANOMA CELLS

The goal of the analysis was to evaluate, whether the administration of other statins with various degrees of hydrophobicity in a combination with Taxol (docetaxel) may increases selectively the Taxol concentration in malignant cells. The tests were carried out using methods described in detail in Example 3.

In the case of pravastatin, its take-up into melanoma cells was not analysed in detail after the analysis of proliferation tests, because of its weak antiproliferative action. Its high hydrophilicity precluded also a complete extraction to the chloroform phase, so in connection with the above, further analysis of pravastatin was abandoned.

The obtained results were summarised in Table 13.

originating from the radial phase (WM35). In the melanoma cells originating from more advanced progression phases, take-ups are higher by 30-45%. Analogically, this effect is connected with a strong inhibition of proliferation of melanoma cells originating from all development phases under the influence of atorvastatin. Taxol retention is a permanent process. A slightly weaker action of fluvastatin characterises correlations between the amount of the docetaxel retained in the melanoma cells under its influence and the proliferation of cells. In both cases, i.e. for atorvastatin and fluvastatin, a synergism of actions occurs; visibly both statins increase the amount of taxanes being accumulated selectively in malignant cells of human melanoma. Rosuvastatin exhibits a weaker effect. Pravastatin, as a strongly hydrophilic molecule, is not able to modify the take-up of taxanes into malignant cells. Considering the data obtained in the first phase of the analyses connected with the influence of simvastatin, and the data obtained in the second phase of the analysis and after taking into account physicochemical properties of the aforementioned pharmaceuticals, one should state that statins having a similar solubility in aqueous solutions irrespective of their chemical structure itself, are able to increase the take-up and block the excretion of taxanes by the cells of human melanoma (solubility of statins in [mg/ml] in water amounts to: 1.23 for atorvastatin,

TABLE 13

Analysis of Taxol take-up into human melanoma cells in the presence of various statins

| | Line name/cell count [mln] | | | | | | | | |
|---|---|---|---|---|---|---|---|---|---|
| | WM 35 35.4 | | | WM239A 34.2 | | | A375P 22.5 | | |
| variables | Integral of the surface area of the absorption spectrum | Taxol concentration [µM]/million of cells | % content in cells | Integral of the surface area of the absorption spectrum | Taxol concentration [µM]/million of cells | % content in cells | Integral of the surface area of the absorption spectrum | Taxol concentration [µM]/million of cells | % content in cells |
| control | 0 | 0 | 0 | 0 | 0 | 0 | 0 | 0 | 0 |
| Docetaxel (T) | 849776 | 57.08/1.61 | 100 | 1114234 | 74.8/2.18 | 100 | 537936 | 36/1.60 | 100 |
| T + atorvastatin | 1798227 | 120/3.39 | 210 | 1471367 | 98.8/2.88 | 132 | 776866 | 52.2/2.32 | 145 |
| T + fluvastatin | 1754994 | 117.9/3.33 | 206 | 1329885 | 89.3/2.6 | 119 | 630477 | 42.4/1.88 | 117 |
| T + rosuvastatin | 1674397 | 112/3.16 | 196 | 1292511 | 86.7/2.53 | 116 | 618626 | 41.4/1.84 | 115 |

Conclusion: Atorvastatin selectively increases the taxanes take-up into human melanoma cells irrespective of the progression phase, from which a given kind of cells originates. Atorvastatin increases the Taxol content in the human melanoma cells by two hundred percent on average in relation to the control with Taxol alone in the melanoma line 0.0886 for rosuvastatin, 0.00046 for fluvastatin, 0.0122 for simvastatin, while for pravastatin, even 19.0). In this case the structural similarity of statins itself is of secondary importance, which has been proved for pravastatin and simvastatin. Both molecules are base on the same structural and spatial scheme. However, they differ significantly in their polarity: simvastatin is highly hydrophobic, while pravastatin is strongly hydrophilic (Log P values, respectively: 4.68 and 0.59). It allows for a general statement that statins having a hydrophobic chemical character will be able to modify the take-up of taxanes into malignant cells of melanoma, as well as other cells originating from ectoderm. Apart from those listed as default, the following statins should be included here: cerivastatin, lovastatin, pitavastatin. For that reason, on should state that hydrophobic statins may be used for preparation of therapeutical composition based on drugs from the taxanes group, such as, e.g., docetaxel or paclitaxel. The therapeutical composition according to the invention should be administered as an infusion or in hydrophobic nanocapsules providing transport to malignant cells, e.g. of human melanoma.

COMPARATIVE EXAMPLE 1. EFFECT OF SIMVASTATIN ADMINISTERED TOGETHER WITH TAXOL ON THE PROLIFERATION AND TOXICITY OF MURINE MELANOMA CELLS

The goal of the analysis was to evaluate, whether the administration of simvastatin in a combination with Taxol (or a treatment regimen including Taxol) may block synergistically the divisions of murine melanoma cells.

The tests were carried out using murine melanoma S91 cell line. The proliferation/cytotoxicity tests were carried out by the "crystal violet" assay and the MTT assay as described in Example 1.

Results of action of a simvastatin-Taxol composition on the proliferation of cells from the S91 cell line, obtained in the "crystal violet" assay are shown in FIG. 2.

Conclusion: The obtained results indicate that in murine melanoma cells from the S91 line, the synergy connected with the influence of simvastatin on the Taxol action does not exist.

COMPARATIVE EXAMPLE 2. EFFECT OF SIMVASTATIN ADMINISTERED TOGETHER WITH TAXOL ON THE PROLIFERATION OF THE COLORECTAL CARCINOMA HT-29 CELL LINE

The goal of the analysis was to evaluate, whether the administration of simvastatin in a combination with Taxol (or a treatment regimen including Taxol) may block synergistically the divisions of HT-29 cells of colorectal carcinoma. The tests were carried out using the colorectal carcinoma HT-29 cell line. The proliferation/cytotoxicity tests were carried out by the "crystal violet" assay and the MTT assay as described in Example 1.

Results of action of a simvastatin-Taxol composition on the proliferation of the colorectal carcinoma HT-29 cells.

The "crystal violet" assay of the effect of simvastatin and Taxol on the proliferation of the colorectal carcinoma HT-29 cells obtained in the "crystal violet" assay are shown in FIG. 3.

Conclusion: Simvastatin does not affect the colorectal carcinoma HT-29 cell line. It does not exhibit synergy with Taxol. The studied cell line is susceptible only to high doses of taxanes.

COMPARATIVE EXAMPLE 3. EFFECT OF SIMVASTATIN ADMINISTERED TOGETHER WITH TAXOL ON THE PROLIFERATION OF HUMAN FIBROBLAST CELLS

The goal of the analysis was to evaluate, whether the administration of simvastatin in a combination with Taxol (or a treatment regimen including Taxol) may block synergistically the divisions of human fibroblast cells. The tests were carried out using a line of human fibroblast cells, i.e., non-malignant cells. The proliferation/cytotoxicity tests were carried out by the "crystal violet" assay and the MTT assay. The results of the "crystal violet" assay of the effect of simvastatin and Taxol on the proliferation of human fibroblast cells are shown in FIG. 2.

TABLE 14

Statistical analysis of the results obtained in the "crystal violet" assay.

| tests | Value of p |
| --- | --- |
| S vs. K | 0.1221 |
| S vs. 25 | 0.0004 |
| S vs. 12.5 | 0.0626 |
| MCT vs. K | 7.24e−07 |
| K vs. z50 | 0.0430 |
| K vs. 25 | 0.5085 |
| K vs. 12.5 | 0.5000 |
| K vs. 6.25 | 0.9482 |
| K vs. 3.12 | 0.4318 |
| K vs. 1.56 | 0.1920 |
| K vs. 0.78 | 0.2505 |
| K vs. 0.39 | 0.2156 |

Conclusion: As it results from the proliferation tests carried out on human fibroblast cells by the "crystal violet" assay, simvastatin in various concentrations, administered with the applied TCM regimen in the dose of 0.5 04, does not affect the normal cells of human skin such as fibroblasts. It is particularly important because of the fact of possible undesirable effects of the applied regimen on other non-malignant human cells.

REFERENCES

1. Dominik, P. K., Cassidy, P. B., Roberts, J. C., (2001). "A new and versatile method for determination of thiolamines of biological importance", J. Chromatogr. B. 761; 1-12.
2. Bronowicka-Adamska, P., Wróbel, M., Zagajewski, J., (2011). "RP-HPLC method for quantitative determination of cystathionine, cysteine and glutathione: An application for the study of the metabolism of cysteine in human brain", Journal of Chromatography B. 879; 2005-2009.
3. Bronowicka-Adamska, P., Wróbel, M., Zagajewski, J., (2015). An application of RP-HPLC for determination of the activity of cystathionine beta-synthase and gamma-cystathionase in tissue homogenates. Nitric Oxide. 46; 186-91.
4. Wróbel, M., Lewandowska, I., Bronowicka-Adamska, P., Paszewski, A., (2009). "The level of sulfane sulfur in The fungus Aspergillus nidulans wild type and mutant strains", Amino Acids. 37; 565-571.
5. Follet J, Corcos L, Baffet G, Ezan F, Morel F, Simon B and Le Jossic-Corcos C (2012), "The association of statins and taxanes: an efficient combination trigger of cancer cell apoptosis", British Journal of Cancer 106, 685-692
6. DeConti R C, Algaz A P, Andrews S, Urbas P, Born O, Stoeckigt D, Floren L, Hwang J, WeberVK J Sondak and Daud A I, (2010), "Phase II trial of sagopilone, a novel epothilone analog in metastatic melanoma", British Journal of Cancer 103, 1548-1553
7. Sarah A. Holstein and Raymond J. Hohl, (2001), "Synergistic Interaction of Lovastatin and Paclitaxel in Human Cancer Cells"; Vol. 1, 141-149, Molecular Cancer Therapeutics 8. Kretzer Iara F; Durvanei A Maria; CGuido Maria, CContente Thais, Maranhao Raul C (2016), "Simvastatinx increases the antineoplastic actions of paclitaxel carried in lipid nanoemulsions in melanoma-bearing mice"; International Journal of Nanomedicine:11 885-904
9. Werner Martin, Atil Bihter, Sieczkowski Evelyn, Chiba Peter, Hohenegger Martin (2013), "Simvastatin-induced compartmentalisation of doxorubicin sharpens up nuclear topoisomerase II inhibition in human rhabdomyosarcoma cells", Arch Phannacol; 386:605-617
10. Meder Janusz, (2011), "Podstawy Onkologii Klinicznej" [Fundamentals of Clinical Oncology], Warsaw.
11. Krzakowski Maciej, Potemski Piotr, Warzocha Krzysztof, Wysocki Piotr, (2014), "Onkologia Kliniczna" [Clinical Oncology]; Gdańsk
12. Holstein S. A., Knapp H. R., Clamon G. H., Murry D. J., Hohl R. J., (2006), "Phannacodynamic effects of high dose lovastatin in subjects with advanced malignancies", Cancer Chemother. Phannacol.; 57: 155-164.
13. van der Spek E., Bloem A. C., van de Donk N. W. et al., (2006) "Dosefinding study of high-dose simvastatin combined with standard chemotherapy in patients with relapsed or refractory myeloma or lymphoma", Haematologica; 91: 542-545.
14. G. N. Schwartz, L. Pendyala, H. Kindler, N. Meropol, R. Perez, D. Raghavan, P. Creaven, "The Clinical Development of Paclitaxel and the Paclitaxel/Carboplatin Combination", Eur. J. Cancer 34(10) 1543-1548, 1998

The invention claimed is:

1. A method of treating human melanoma, comprising administering a taxane and a hydrophobic statin to a human in need thereof, wherein the statins are selected from the group consisting of simvastatin, atorvastatin, fluvastatin, rosuvastatin, cerivastatin, lovastatin, pravastatin, and mixtures thereof.

2. The method of claim 1, wherein the hydrophobic statin is selected from the group consisting of simvastatin, atorvastatin, fluvastatin, rosuvastatin, and mixtures thereof.

3. The method of claim 1, wherein the hydrophobic statin is simvastatin.

4. The method of claim 1, wherein the taxane is paclitaxel or docetaxel.

5. The method of claim 1, wherein the taxane is paclitaxel.

6. The method of claim 1, wherein a composition comprising the taxane and the hydrophobic statin is administered.

7. The method of claim 1, wherein a composition comprising the taxane is administered and a separate composition comprising the hydrophobic statin is administered.

8. The method of claim 1, wherein administering taxane and the hydrophobic statin to the human in need thereof treats human melanoma and provides palliation of symptoms connected with embolic-thrombotic complications and neoplastic disease.

9. The method of claim 1, wherein an aqueous solution comprising simvastatin and a mixture of cytostatic drugs including the taxane is administered.

10. The method of claim 9, wherein the mixture of cytostatic drugs consists of a taxane, cisplatin and melphalan.

* * * * *

UNITED STATES PATENT AND TRADEMARK OFFICE
CERTIFICATE OF CORRECTION

PATENT NO. : 10,912,756 B2  
APPLICATION NO. : 16/479397  
DATED : February 9, 2021  
INVENTOR(S) : Wojciech Placha et al.

Page 1 of 1

It is certified that error appears in the above-identified patent and that said Letters Patent is hereby corrected as shown below:

On the Title Page

At item (71) delete "Crakow" and insert --Kracow--

At item (73) delete "Crakow" and insert --Kracow--

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*